US00PP29204P3

(12) United States Plant Patent
Probst

(10) Patent No.: US PP29,204 P3
(45) Date of Patent: Apr. 3, 2018

(54) ***COREOPSIS* PLANT NAMED 'PROISE'**

(50) Latin Name: ***Coreopsis hybrida*/Tickseed Plant**
Varietal Denomination: Proise

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 0 days.

(21) Appl. No.: 14/757,511

(22) Filed: Dec. 23, 2015

(65) Prior Publication Data

US 2017/0188502 P1 Jun. 29, 2017

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

PUBLICATIONS

Aris Green Leaf Plants Perennials, Grasses & Herbs 2015/2016, retrieved on Apr. 10, 2017, retrieved from the Internet at <http://www.glplants.com/system/cms/files/files/000/000/597/original/15015_GL_Perennial_Catalog_WEB-SEQ_SMALL_72-MAX.pdf> pp. 1-5 and 16.*

* cited by examiner

*Primary Examiner* — June Hwu
(74) *Attorney, Agent, or Firm* — Buchanan Ingersoll & Rooney PC

(57) ABSTRACT

The present *Coreopsis* variety was created during a controlled plant breeding program. A compact and bushy growth habit is displayed. Attractive, large burgundy to purple daisy-type inflorescences are formed in abundance with near white apices on the ray florets during warm growing conditions. The dark green foliage coloration contrasts nicely with the blossom coloration. Excellent resistance to powdery mildew has been displayed during observations to date. The plant is a perennial and has been observed to be hardy to at least U.S.D.A. Hardiness Zone No. 5. The plant can be grown to advantage as attractive ornamentation in parks, gardens, and residential settings.

2 Drawing Sheets

Botanical/commercial classification: *Coreopsis hybrida*/Tickseed Plant.
Varietal denomination: cv. Proise.

SUMMARY OF THE INVENTION

Plants of *Coreopsis* sometimes bear a common name such as Tickseed, and are recognized to be ornamental herbaceous plants for landscape or container uses.

The new variety of *Coreopsis* hybrid was created from an ongoing controlled breeding program in 2010 in Hubbardston, Mass., U.S.A. The objective of the breeding program was to develop new varieties having superior attributes that are long-lived, exhibit a perennial habit to at least U.S.D.A. Hardiness Zone No. 5, and display an array of attractive flower colorations and plant forms. The female parent (i.e., the seed parent) of the new variety was an unnamed, unreleased, and non-patented *Coreopsis* plant designed Q2 09-7. Pollen used for the cross was pooled from a mixture of unnamed, unreleased, and non-patented *Coreopsis* plants that displayed limited fertility with the formation of a limited quantity of pollen. The exact male parent that contributed to the origin of the new cultivar is unknown.

It was found that the new *Coreopsis* plant displays the following combination of characteristics:

(a) displays a compact and bushy growth habit,
(b) displays in abundance attractive large burgundy to purple inflorescences with near white apices on the ray florets during warm growing conditions, (c) exhibits excellent resistance to powdery mildew, and
(d) is hardy to at least U.S.D.A. Hardiness Zone No. 5.

The expressed combination of characteristics enables the new cultivar to be readily distinguished from the 'Mercury Rising' cultivar (U.S. Plant Pat. No. 24,689). More specifically, the new cultivar commonly displays a larger flower size and a more compact growth habit. Also, the new cultivar under warm growing temperatures tends to develop more uniformly and to a greater degree more near white/yellow coloration on the upper petal surfaces at the apices than the 'Mercury Rising' cultivar.

Additionally, the new variety can be readily distinguished from its ancestors. More specifically, the female parent (i.e., the seed parent), *Coreopsis* plant designed Q2 09-7 displays white flowers with a rose-purple edge and is very fertile producing an abundance of seeds, whereas the new variety displays burgundy to purple colored flowers and is sterile.

The new cultivar can be grown in the ground or in a container to provide attractive ornamentation in parks, gardens, and residential settings.

Asexual reproduction of the new cultivar in a controlled environment by the rooting of vegetative cuttings, such as stem cuttings (e.g., terminal tip cuttings), has been conducted at West Grove, Pa., U.S.A. It has been demonstrated that the combination of characteristics of the new cultivar is firmly fixed and is well retained in succeeding generations. Accordingly, the new cultivar can be asexually reproduced in a true-to-type manner. The new cultivar also can be asexually propagated by division.

The new cultivar has been named 'Proise'.

BRIEF DESCRIPTION OF THE PHOTOGRAPHS

The accompanying photographs illustrate typical flowering plants of the new variety at an age of approximately two years. The plants had been asexually reproduced by the use of vegetative cuttings, such as stem cuttings (e.g., terminal tip cuttings), and were growing outdoors on its own roots in the ground in full sun during June 2014 at West Grove, Pa., U.S.A.

DETAILED BOTANICAL DESCRIPTION

The chart used in the identification of the colors described herein is The R.H.S. Colour Chart of The Royal Horticultural Society, London, England (1995 Edition). The plants had been asexually reproduced by the rooting of vegetative cuttings, such as stem cuttings (e.g., terminal tip cuttings), were approximately two years of age, and were observed during June while growing in containers at West Grove, Pa., U.S.A.

Botanical classification: *Coreopsis hybrida.*

Figure 1:
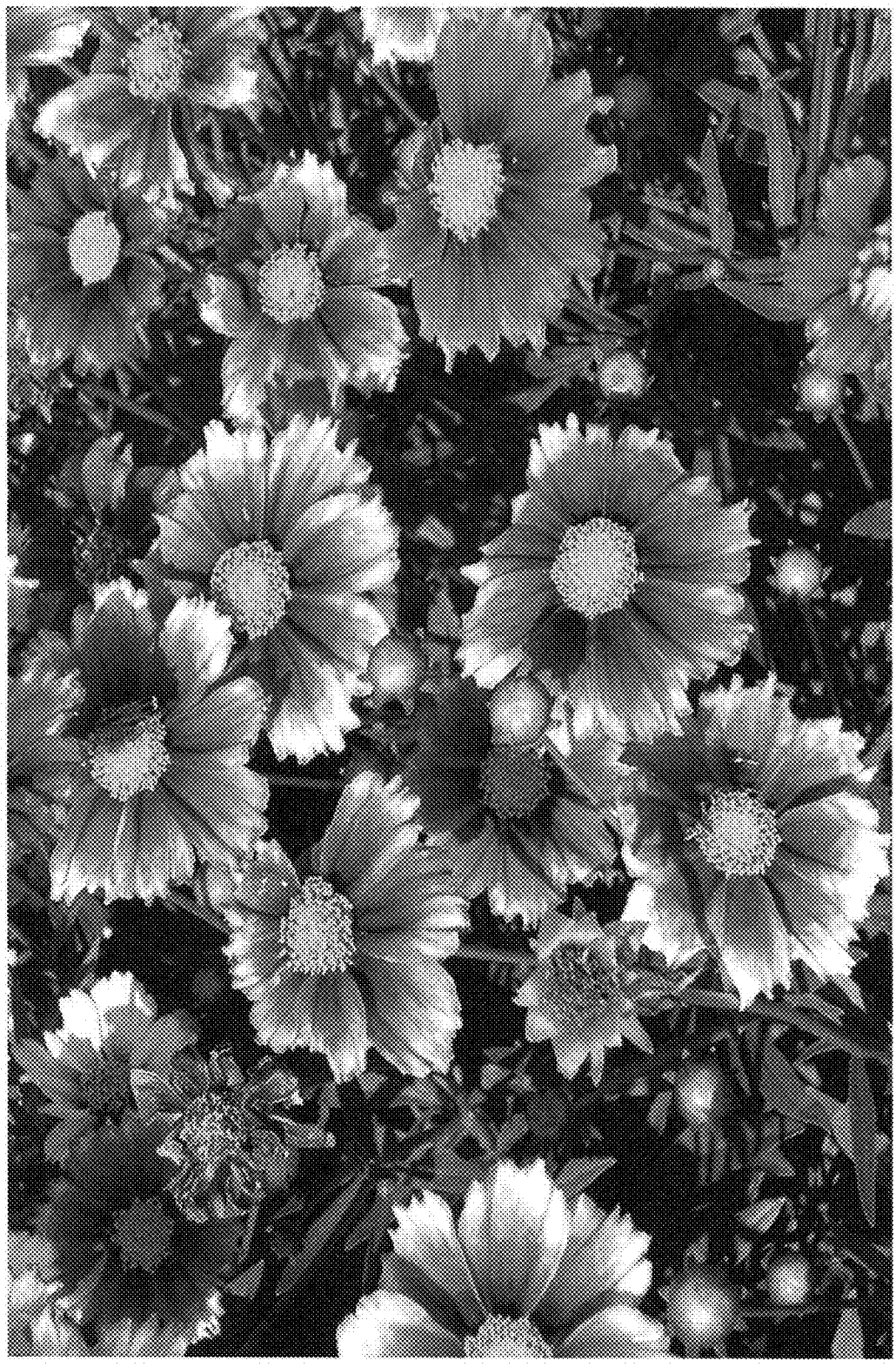
FIG. 1 shows a close view of the attractive burgundy to purple florescences of the new cultivar where in the ray florets display near white apices.
Figure 2:
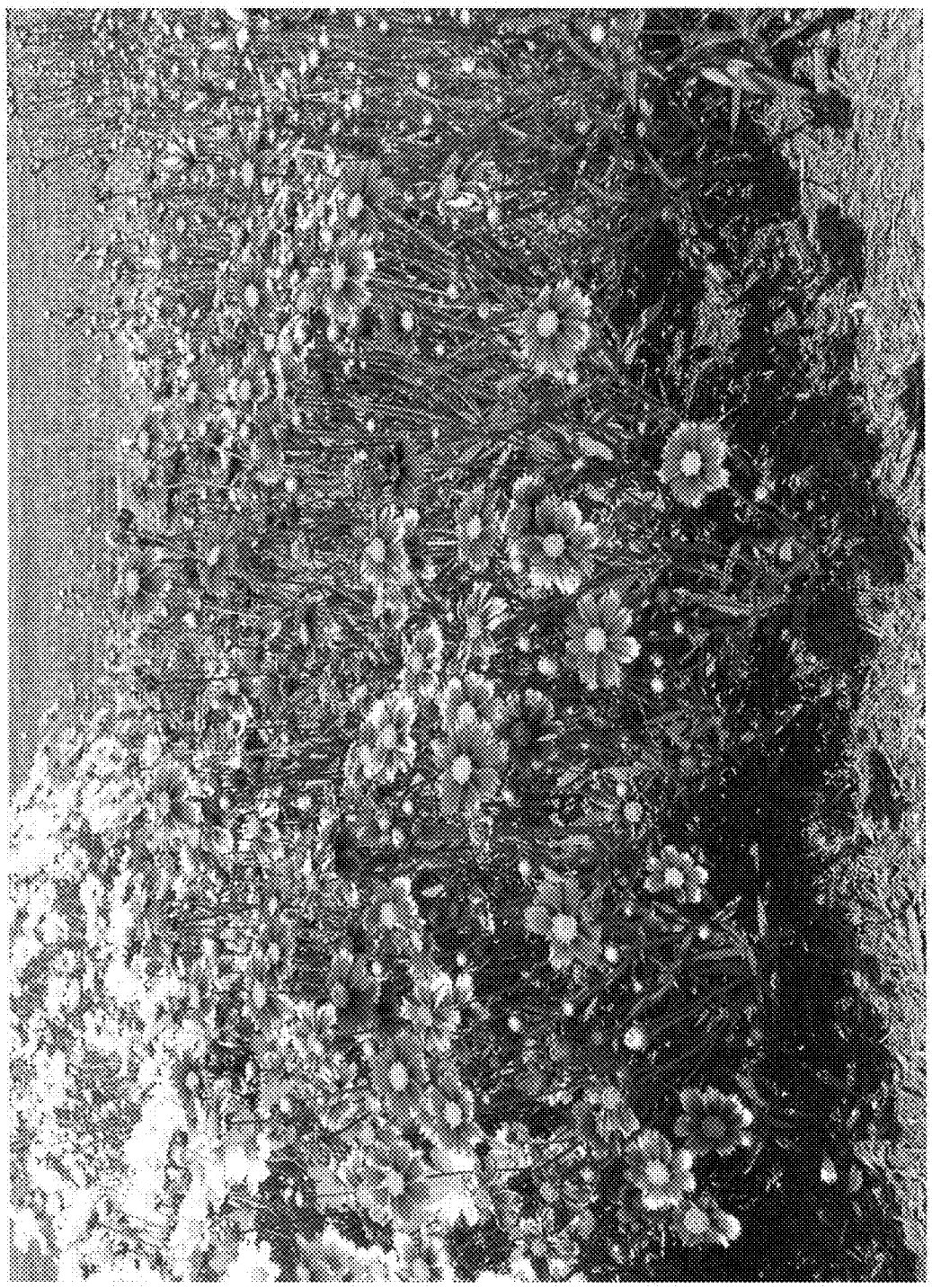
FIG. 2 shows the compact and bushy growth habit of flowering plants of the new cultivar.

Cultivar: Proise.

Plant:

*Habit.*—Vigorous herbaceous perennial, compact and bushy, clump-forming with sturdy stems and an upright and spreading canopy.

*Height.*—Approximately 50 cm on average. This compares to approximately 63 cm on average for the 'Mercury Rising' cultivar under the same growing conditions.

*Width.*—Approximately 65 cm on average. This compares to approximately 67.5 cm on average for the 'Mercury Rising' cultivar under the same growing conditions.

*Branching.*—Highly branched, commonly with approximately 10 basal branches on average and approximately 2 to 5 secondary branches on average.

*Branch internodes.*—Arise opposite at nodes, variable, and typically approximately 6 cm in length.

*Stem shape.*—Substantially round and wiry.

*Stem length.*—Main stems commonly are approximately 20 cm in length on average with laterals of approximately 9 cm in length (excluding peduncles).

*Stem diameter.*—Main stems commonly are approximately 7 mm in diameter on average.

*Stem texture.*—Glabrous when young and commonly ridged with minute generally translucent pubescence when mature.

*Stem color.*—Near Green Group 137A.

*Roots.*—Fibrous, fine, and well branched.

Foliage:

*Arrangement.*—Opposite, single, sessile.

*Configuration.*—Simple with tri-fid and five-fid upper leaves, lanceolate, and with lanceolate secondary lobes.

*Length.*—Variable, up to approximately 14 cm in length on average, and secondary lobes commonly average approximately 4 cm in length.

*Width.*—Variable, and up to 2.5 cm in width for a primary lobe, and secondary lobes commonly are approximately 1.3 cm in width on average.

*Apex.*—Narrowly acute.

*Base.*—Attenuate.

*Margin.*—Primarily entire with some leaves having secondary lobes often disposed substantially horizontal to the primary lobe.

*Texture.*—Dull with fine pubescence on the upper and under surfaces commonly combined with slight undulation.

*Venation.*—Non-conspicuous, pinnate, and of substantially the same coloration as the foliage on both surfaces, near Green Group 137B.

*Color.*—Young leaves: near Green Group 137A on the upper surface, and near Green Group 137B on the under surface. Mature leaves: near Green Group 137A on the upper surface, and near Green Group 137A on the under surface.

Flower description:

*Quantity.*—When grown in a one-gallon container commonly 90 flowers are displayed at a time.

*Bud shape.*—Generally spherical.

*Bud size.*—Approximately 9 mm in length and diameter on average.

*Bud color.*—Near Yellow Group 7A, and covered with bracts of Yellow-Green Group 146A and 146B.

*Flower appearance.*—Large daisy-type composite inflorescence form with elongated oblong-shaped ray florets and disc florets at the center forming a radiant head. Inflorescences are borne on terminals arising from leaf axils.

*Lastingness.*—Commonly approximately one week until senescence of ray florets while disc florets and bracts tend to be persistent.

*Flowering response.*—Under normal conditions, plants flower from June to August in southeastern Pennsylvania, U.S.A.

*Inflorescence diameter.*—Commonly up to about 6.5 cm on average when fully open.

*Inflorescence depth.*—Commonly up to approximately 1.2 cm on average when open.

*Disc.*—Commonly up to approximately 1.3 cm in diameter on average.

*Fragrance.*—Slightly acrid when crushed.

*Ray florets.*—Aspect: held slightly cupped upward when opening and becoming nearly horizontal at maturity, and emarginated in three longitudinal sections with the central section being the longest. Shape: broadly oblanceolate. Length: approximately 2.5 cm on average. Width: approximately 1 cm on average. Apex: notched. Base: broadly cuneate. Margin: entire. Texture: glabrous on both surfaces. Number: approximately eight arranged in a single whorl. Color when opening: under warm growing conditions are commonly near Yellow Group 4B with ribs on petals that are commonly near Yellow Group 5B. Color when fully open: under warm growing conditions on the upper surfaces are near Red-Purple Group 59A, with the bases commonly near Greyed-Purple Group 187B, blending to near Yellow Group 4D at the apices and on the under surface near Yellow Group 11C, and under cool growing conditions on the upper surfaces are near Red-Purple Group 59C and on the under surfaces near Yellow Group 11C suffused with Red-Purple Group 59A away from the apex. The new cultivar under warm growing conditions has been found to develop more uniformly on the upper petal surfaces at the petal apices more near white/yellow coloration than the 'Mercury Rising' cultivar. Also, upper petal apices of the 'Mercury Rising' cultivar to the extent lightened in coloration have been observed to be near Yellow Group 2B.

*Disc florets*.—Arrangement: massed at the center of the inflorescence. Shape: tubular, fused at the base, and flared at the apex. Length: commonly approximately 6 mm on average. Width: commonly approximately 1.3 mm on average at the base. Color: near Yellow-Green Group 153A when immature, near Yellow-Orange Group 17B when fully open, becoming near Brown Group 200D when dried as the ray florets drop. The base is near Yellow-Green Group 144D with a flared portion of near Yellow-Orange Group 17D and somewhat translucent.

*Reproductive organs*.—Location: androecium and gynoecium present only among disc florets. Stamen number: five per floret fused into a tube surrounding the style. Anther size: approximately 3 mm in length on average, and approximately 0.7 mm in width on average. Anther color: near Greyed-Orange Group 165A. Pollen quantity: sparsely produced during observations to date. Pistil number: one per floret. Pistil length: approximately 4 mm on average. Style appearance: very fine. Style color: near Yellow-Green Group 152D and somewhat translucent. Stigma shape: bifid and pilose, with recurved branches approximately 1.5 mm in length. Stigma color: commonly near Yellow-Orange Group 17B. Ovary size: commonly approximately 2 mm in length on average, and approximately 1 mm in width on average. Ovary color: near Yellow-Green Group 145D. Receptacle size: approximately 2 mm in depth on average and approximately 4 cm in diameter on average. Receptacle color: near Yellow-Green Group 144D. Seeds/fruit: none encountered during observation to date.

*Involucral bracts*.—Number: commonly in two rows of eight. Arrangement: the outer bracts are unfused and somewhat reflexed when the flower is fully open and becoming substantially horizontal after the ray florets drop. The inner bracts overlap and surround the receptacle in a campanulate form with the apical portion unfused and spreading and held close to the ray florets. Shape: the outer bracts are lanceolate and the free portions of the inner bracts are broadly lanceolate. Size: outer bracts commonly up to 6 mm in length and 2 mm in width at the widest point, and inner bracts approximately 1 cm in length and 3 mm in width with a free portion approximately 8 mm in length and approximately 3 mm in width. Apex: narrowly acute on outer bracts and apiculate on inner bracts. Texture: outer bracts are puberulent and the inner bracts are waxy. Margins: entire on the inner and outer bracts. Color: outer bracts are near Green Group 138A on both surfaces, the fused portion of the inner bracts is near Yellow-Green Group 147B, the unfused portion of the inner bracts is near Yellow-Green Group 147B, and the center, apex and margin are near Yellow-Green Group 153B.

*Peduncles*.—Strength: relatively strong. Size: commonly approximately 9 cm in length on average, and approximately 1.5 mm in diameter on average. Texture: glabrous. Color: commonly near Green Group 137A.

Disease resistance: Excellent with respect to powdery mildew, such as *Sphaerotheca macularis*, during observations to date. This resistance has been observed to exceed that commonly displayed by other large-flowered *Coreopsis* grandiflora plants grown under the same conditions.

Hardiness: Hardy to at least U.S.D.A. Hardiness Zone No. 5 (e.g., Nos. 5 to 9) during observations to date.

Propagation: Through the rooting of vegetative cuttings, including stem cuttings (e.g., terminal tip cuttings), or by division.

Plants of the new 'Proise' cultivar have not been observed under all possible environmental conditions to date. Accordingly, it is possible that the phenotypic expression may vary somewhat with changes in light intensity and duration, cultural practices, and other environmental conditions.

I claim:

1. A new and distinct *Coreopsis* plant having the following combination of characteristics:

(a) displays a compact and bushy growth habit, (b) displays in abundance large burgundy to purple inflorescences with near white apices on the ray florets during warm growing conditions, (c) exhibits excellent resistance to powdery mildew, and (d) is hardy to at least U.S.D.A. Hardiness Zone No. 5;

substantially as illustrated and described.

* * * * *